(12) United States Patent
Gainor et al.

(10) Patent No.: US 11,331,105 B2
(45) Date of Patent: May 17, 2022

(54) DIFFUSION RESISTANT IMPLANTABLE DEVICES FOR REDUCING PULSATILE PRESSURE

(71) Applicant: Aria CV, Inc., St. Paul, MN (US)

(72) Inventors: John Gainor, Mendota Heights, MN (US); Karl Vollmers, Minneapolis, MN (US); John Scandurra, Saint Paul, MN (US); Lucas Harder, Minneapolis, MN (US); Piramiah Elayaperumal, Woodbury, MN (US)

(73) Assignee: Aria CV, Inc., St. Paul, MN (US)

(*) Notice: Subject to any disclaimer, the term of this patent is extended or adjusted under 35 U.S.C. 154(b) by 274 days.

(21) Appl. No.: 16/342,968

(22) PCT Filed: Oct. 17, 2017

(86) PCT No.: PCT/US2017/057035
§ 371 (c)(1),
(2) Date: Apr. 17, 2019

(87) PCT Pub. No.: WO2018/075552
PCT Pub. Date: Apr. 26, 2018

(65) Prior Publication Data
US 2020/0046369 A1    Feb. 13, 2020

Related U.S. Application Data

(60) Provisional application No. 62/410,232, filed on Oct. 19, 2016.

(51) Int. Cl.
*A61B 17/12*    (2006.01)
*A61L 29/12*    (2006.01)
(Continued)

(52) U.S. Cl.
CPC .. *A61B 17/12136* (2013.01); *A61B 17/12036* (2013.01); *A61B 17/12109* (2013.01);
(Continued)

(58) Field of Classification Search
CPC ........ A61B 17/12136; A61B 17/12036; A61B 17/12109; A61B 2017/00849;
(Continued)

(56) References Cited

U.S. PATENT DOCUMENTS 3,275,001 A    9/1966  Rosecrans
3,634,924 A    1/1972  Blake et al.
(Continued)

FOREIGN PATENT DOCUMENTS

CN    102657910.1 A    9/2012
CN    103260547 A    8/2013
(Continued)

OTHER PUBLICATIONS

U.S. Appl. No. 13/701,721 / U.S. Pat. No. 9,987,153, filed May 31, 2011 / Jun. 5, 2018.
(Continued)

*Primary Examiner* — Shaun L David
(74) *Attorney, Agent, or Firm* — Eversheds Sutherland (US) LLP; Christopher C. Bolten; Albert K. Heng

(57) ABSTRACT

A device for reducing pulsatile pressure within a vessel to treat heart disease, such as pulmonary hypertension, includes a compliant body structured to expand and contract upon changes in pressure within the vessel, a reservoir structured for holding a fluid therein, and a conduit extending between and fluidly coupling the reservoir and the compliant body, wherein the device includes a graphene-polymer composite designed to resist diffusion of the fluid through the device.

25 Claims, 6 Drawing Sheets

(51) Int. Cl.
*A61M 39/02* (2006.01)
*A61B 17/00* (2006.01)

(52) U.S. Cl.
CPC ....... *A61L 29/123* (2013.01); *A61M 39/0208* (2013.01); *A61B 2017/00849* (2013.01); *A61B 2017/00893* (2013.01); *A61B 2017/00964* (2013.01)

(58) Field of Classification Search
CPC ........... A61B 2017/00893; A61B 2017/00964; A61B 2090/063; A61B 2090/064; A61L 29/123; A61L 29/103; A61L 31/122; A61M 39/0208; A61M 60/135; A61M 60/40; A61M 60/869
See application file for complete search history.

(56) References Cited

U.S. PATENT DOCUMENTS

| | | |
|---|---|---|
| 3,818,903 A | 6/1974 | Bleecker |
| 4,422,447 A | 12/1983 | Schiff |
| 4,793,351 A | 12/1988 | Landman et al. |
| 4,902,273 A | 2/1990 | Choy et al. |
| 4,938,766 A | 7/1990 | Jarvik |
| 4,955,905 A | 9/1990 | Reed |
| 5,002,531 A | 3/1991 | Bonzel |
| 5,112,303 A | 5/1992 | Pudenz et al. |
| 5,222,980 A | 6/1993 | Gealow |
| 5,409,444 A | 4/1995 | Kensey et al. |
| 5,496,311 A | 3/1996 | Abele et al. |
| 5,578,085 A | 11/1996 | Johnson, Jr. et al. |
| 5,713,867 A | 2/1998 | Morris |
| 5,769,821 A | 6/1998 | Abrahamson et al. |
| 5,795,325 A | 8/1998 | Valley et al. |
| 5,814,016 A | 9/1998 | Valley et al. |
| 5,820,542 A | 10/1998 | Dobak et al. |
| 5,833,655 A | 11/1998 | Freed et al. |
| 6,017,324 A | 1/2000 | Tu et al. |
| 6,030,336 A | 2/2000 | Franchi |
| 6,053,891 A | 4/2000 | Decampli |
| 6,136,025 A | 10/2000 | Barbut et al. |
| 6,210,318 B1 | 4/2001 | Lederman |
| 6,261,304 B1 | 7/2001 | Hall et al. |
| 6,461,367 B1 | 10/2002 | Kirsch et al. |
| 6,558,349 B1 | 5/2003 | Kirkman |
| 6,559,349 B1 | 5/2003 | Slaugh et al. |
| 6,576,007 B2 | 6/2003 | Dehdashtian et al. |
| 6,579,224 B1 | 6/2003 | Burton et al. |
| 6,682,473 B1 | 1/2004 | Matsuura et al. |
| 7,044,967 B1 | 5/2006 | Solem et al. |
| 7,074,178 B2 | 7/2006 | Connors et al. |
| 7,468,050 B1 | 12/2008 | Kantrowitz |
| 7,540,876 B2 | 6/2009 | Connors et al. |
| 7,766,814 B2 | 8/2010 | Walsh |
| 7,811,249 B2 | 10/2010 | Saab |
| 7,928,367 B2 | 4/2011 | Hirota et al. |
| 8,016,740 B2 | 9/2011 | Connors et al. |
| 8,092,521 B2 | 1/2012 | Figulla et al. |
| 8,116,883 B2 | 2/2012 | Williams et al. |
| 8,206,378 B1 | 6/2012 | Kalpin et al. |
| 8,585,572 B2 | 11/2013 | Mehmanesh |
| 8,747,386 B2 | 6/2014 | Rykhus et al. |
| 8,876,850 B1 * | 11/2014 | Vollmers ............. A61M 5/1723 606/194 |
| 8,882,653 B2 | 11/2014 | Gillespie, Jr. et al. |
| 8,956,379 B2 | 2/2015 | Luciano et al. |
| 9,017,359 B2 | 4/2015 | Scandurra et al. |
| 9,039,725 B1 | 5/2015 | Vollmers et al. |
| 9,107,992 B2 | 8/2015 | Kushwaha et al. |
| 9,242,082 B2 | 1/2016 | Vollmers et al. |
| 9,333,328 B2 | 5/2016 | Scandurra et al. |
| 9,610,391 B2 | 4/2017 | Vollmers et al. |
| 9,801,989 B2 | 10/2017 | Vollmers et al. |
| 9,987,153 B2 | 6/2018 | Scandurra et al. |
| 10,327,880 B2 | 6/2019 | Connors et al. |
| 10,376,681 B2 | 8/2019 | Bak-Boychuk et al. |
| 10,682,448 B2 | 6/2020 | Vollmers et al. |
| 10,702,682 B2 | 7/2020 | Scandurra et al. |
| 10,751,519 B2 | 8/2020 | Scandurra et al. |
| 2001/0023332 A1 | 9/2001 | Hahnen |
| 2003/0055465 A1 | 3/2003 | Ben-Haim et al. |
| 2003/0208259 A1 | 11/2003 | Penhasi |
| 2004/0093007 A1 | 5/2004 | Sussman et al. |
| 2004/0106971 A1 | 6/2004 | Schwartz et al. |
| 2004/0111006 A1 | 6/2004 | Alferness et al. |
| 2004/0143319 A1 | 7/2004 | Schwartz et al. |
| 2004/0210304 A1 | 10/2004 | Seguin et al. |
| 2005/0015107 A1 | 1/2005 | O'Brien |
| 2005/0059965 A1 | 3/2005 | Eberl et al. |
| 2005/0070938 A1 | 3/2005 | Copa et al. |
| 2005/0131451 A1 | 6/2005 | Kleshinski et al. |
| 2005/0267596 A1 | 12/2005 | Chen et al. |
| 2006/0085028 A1 | 4/2006 | Boock |
| 2006/0093642 A1 * | 5/2006 | Ranade ................ A61L 29/103 424/423 |
| 2006/0106450 A1 | 5/2006 | Ben Muvhar |
| 2006/0129083 A1 | 6/2006 | Brenneman et al. |
| 2006/0135962 A1 | 6/2006 | Kick et al. |
| 2006/0155310 A1 | 7/2006 | Binmoeller |
| 2006/0241745 A1 | 10/2006 | Solem |
| 2006/0253095 A1 | 11/2006 | Stull |
| 2007/0142819 A1 | 6/2007 | El-Nounou et al. |
| 2007/0156013 A1 | 7/2007 | Birk |
| 2007/0156167 A1 | 7/2007 | Connors et al. |
| 2007/0293848 A1 * | 12/2007 | Endo .................... A61B 17/00 606/1 |
| 2008/0114338 A1 | 5/2008 | Kumar |
| 2008/0132750 A1 | 6/2008 | Miller |
| 2008/0147181 A1 | 6/2008 | Ghione et al. |
| 2008/0194905 A1 | 8/2008 | Walsh |
| 2008/0195174 A1 | 8/2008 | Walker et al. |
| 2008/0243093 A1 | 10/2008 | Kalpin et al. |
| 2008/0312679 A1 | 12/2008 | Hardert et al. |
| 2009/0143837 A1 | 6/2009 | Rossing et al. |
| 2009/0222083 A1 | 9/2009 | Nguyen et al. |
| 2009/0240277 A1 | 9/2009 | Connors et al. |
| 2009/0294031 A1 | 12/2009 | Pepper et al. |
| 2010/0042070 A1 | 2/2010 | Gill et al. |
| 2010/0099945 A1 | 4/2010 | Birk et al. |
| 2010/0185049 A1 | 7/2010 | Birk et al. |
| 2010/0197994 A1 | 8/2010 | Mehmanesh |
| 2010/0204590 A1 | 8/2010 | Hatib et al. |
| 2010/0274221 A1 | 10/2010 | Sigg et al. |
| 2010/0324472 A1 | 12/2010 | Wulfman |
| 2010/0331767 A1 | 12/2010 | Frankowski et al. |
| 2011/0124951 A1 | 5/2011 | Walsh |
| 2011/0137210 A1 | 6/2011 | Johnson |
| 2011/0137428 A1 | 6/2011 | Terliuc |
| 2012/0053514 A1 | 3/2012 | Robinson et al. |
| 2012/0083646 A1 | 4/2012 | Benson |
| 2012/0172654 A1 | 7/2012 | Bates |
| 2013/0079871 A1 | 3/2013 | Scandurra et al. |
| 2013/0165964 A1 | 6/2013 | Vollmers et al. |
| 2013/0245665 A1 | 9/2013 | Scandurra et al. |
| 2014/0214149 A1 | 7/2014 | Kuraguntla et al. |
| 2014/0228878 A1 | 8/2014 | Scandurra et al. |
| 2014/0370246 A1 * | 12/2014 | Hurt .................... B32B 37/14 428/189 |
| 2015/0196303 A1 | 7/2015 | Seguin |
| 2015/0216531 A1 | 8/2015 | Seguin |
| 2015/0282859 A1 | 10/2015 | Bencini et al. |
| 2015/0352335 A1 * | 12/2015 | Moeller .............. A61M 25/104 606/194 |
| 2015/0366652 A1 | 12/2015 | Connors |
| 2016/0144091 A1 * | 5/2016 | Breedon .............. A61M 60/148 623/3.29 |
| 2016/0237237 A1 * | 8/2016 | Tour .................... C08L 75/04 |
| 2016/0310306 A1 | 10/2016 | Brister et al. |
| 2020/0306435 A1 | 10/2020 | Vollmers et al. |

(56) References Cited

U.S. PATENT DOCUMENTS

| | | | |
|---|---|---|---|
| 2020/0368507 A1 | 11/2020 | Scandurra et al. | |
| 2021/0069396 A1 | 3/2021 | Vollmers et al. | |

FOREIGN PATENT DOCUMENTS

| | | | | |
|---|---|---|---|---|
| DE | 19508129 A1 | 9/1996 | | |
| DE | 19508129 C2 | 2/1997 | | |
| DE | 10 2005 060 197 A1 | 6/2007 | | |
| EP | 0 366 814 A1 | 5/1990 | | |
| EP | 0 959 912 B1 | 12/1999 | | |
| EP | 0959912 B1 | 9/2004 | | |
| EP | 2 016 961 B1 | 1/2009 | | |
| EP | 2016961 B1 | 2/2010 | | |
| FR | 3017044 A1 | 8/2015 | | |
| FR | 3016279 A1 | 7/2017 | | |
| JP | 2005538807 A | 12/2005 | | |
| JP | 2007526039 A | 9/2007 | | |
| JP | 2009502247 A | 1/2009 | | |
| JP | 2009509650 A | 3/2009 | | |
| WO | WO-90/04430 A1 | 5/1990 | | |
| WO | WO-90/06086 A1 | 6/1990 | | |
| WO | WO-93/17731 A1 | 9/1993 | | |
| WO | WO-95/10317 A1 | 4/1995 | | |
| WO | WO-95/32018 A1 | 11/1995 | | |
| WO | WO-96/00095 A1 | 1/1996 | | |
| WO | WO-96/12518 A1 | 5/1996 | | |
| WO | WO-96/34647 A1 | 5/1996 | | |
| WO | WO-98/50100 A1 | 11/1998 | | |
| WO | WO-99/04833 | 2/1999 | | |
| WO | WO-00/66030 A1 | 11/2000 | | |
| WO | WO-02/36048 | 5/2002 | | |
| WO | WO-2004/026112 A2 | 4/2004 | | |
| WO | WO-2004/080338 A2 | 9/2004 | | |
| WO | WO-2005/084730 A1 | 9/2005 | | |
| WO | WO-2006/020942 A1 | 2/2006 | | |
| WO | WO-2006/067473 A1 | 6/2006 | | |
| WO | WO-2007/014028 A1 | 2/2007 | | |
| WO | WO-2007/038476 A2 | 4/2007 | | |
| WO | WO-2007/059594 A1 | 5/2007 | | |
| WO | WO-2008/154145 A1 | 12/2008 | | |
| WO | WO-2010/022173 A1 | 2/2010 | | |
| WO | WO-2010/129089 A4 | 11/2010 | | |
| WO | WO-2010129089 A4 | 3/2011 | | |
| WO | WO-2012/071395 A1 | 5/2012 | | |
| WO | WO-2013/109891 A | 7/2013 | | |
| WO | WO-2013/148697 A1 | 10/2013 | | |
| WO | WO-2013/185138 A1 | 12/2013 | | |
| WO | WO-2015/107434 A1 | 7/2015 | | |
| WO | WO-2015102693 A2 * | 7/2015 | ............. | C08L 75/04 |
| WO | WO-2015/114471 A1 | 8/2015 | | |
| WO | WO-2015/133849 A1 | 9/2015 | | |
| WO | WO-2018075552 A1 | 4/2018 | | |

OTHER PUBLICATIONS

U.S. Appl. No. 13/884,169 / U.S. Pat. No. 9,017,359, filed Nov. 22, 2011 / Apr. 28, 2015.
U.S. Appl. No. 14/253,127 / U.S. Pat. No. 9,333,328, filed Apr. 15, 2014 / May 10, 2016.
U.S. Appl. No. 14/309,758 / U.S. Pat. No. 8,876,850, filed Jun. 19, 2014 / Nov. 4, 2014.
U.S. Appl. No. 14/531,846 / U.S. Pat. No. 9,039,725, filed Nov. 3, 2014 / May 26, 2015.
U.S. Appl. No. 14/710,180 / U.S. Pat. No. 9,242,082, filed May 12, 2015 / Jan. 26, 2016.
U.S. Appl. No. 14/955,109, filed Dec. 1, 2015.
U.S. Appl. No. 14/956,127, filed Dec. 1, 2015.
U.S. Appl. No. 14/990,627 / U.S. Pat. No. 9,610,391, filed Jan. 7, 2016 / Apr. 4, 2017.
U.S. Appl. No. 15/474,902 / U.S. Pat. No. 9,801,989, filed Mar. 30, 2017 / Oct. 31, 2017.
U.S. Appl. No. 15/785,304, filed Oct. 16, 2017.
U.S. Appl. No. 15/993,572, filed May 30, 2018.
U.S. Appl. No. 16/288,088, filed Feb. 27, 2019.
Borlaug, B. A., & Kass, D. A. (2008). Ventricular-Vascular Interaction in Heart Failure. Heart Failure Clinics, 4(1), 23-36.
Elzinga, G., & Westerhof, N. (1973). Pressure and flow generated by the left ventricle against different impedances. Circulation Research, 32(2), 178-186.
Elzinga, G., et al., (1980). Left and right ventricular pump function and consequences of having two pumps in one heart. Circ Res, 46, 564-574.
Extended EP Search Report dated Feb. 6, 2018 in EP Patent Appl. Serial No. 11843546.0.
Extended EP Search Report dated Mar. 1, 2017 in EP Patent Application Serial No. 11792905.9.
Grant, B. J. B., & Lieber, B. B. (1996). Clinical significance of pulmonary arterial input impedance. European Respiratory Journal, 9(11), 2196-2199.
Harnek, Jan, et al. "Transcatheter implantation of the MONARC coronary sinus device for mitral regurgitation: 1-year results from the Evolution phase I study (Clinical Evaluation of the Edwards Lifesciences Percutaneous Mitral Annuloplasty System for the Treatment of Mitral Regurgitation)." JACC: Cardiovascular Interventions 4.1 (2011): 115-122.
International Search Report & Written Opinion dated Dec. 22, 2015 in Int'l PCT Patent Application Serial No. PCT/US2015/036201.
International Search Report & Written Opinion for PCT/US2017/057035 dated Jan. 31, 2018.
International Search Report dated Sep. 8, 2011 in PCT Patent Appl No. PCT/US2011/38558.
Lammers, S. et al.,(2012). Mechanics and function of the pulmonary vasculature: implications for pulmonary vascular disease and right ventricular function. Comprehensive Physiology.
Lankhaar, J. W., et al.(2008). "Pulmonary vascular resistance and compliance stay inversely related during treatment of pulmonary hypertension." European heart journal.
Mahapatra, S. et al., (2006). Relationship of pulmonary arterial capacitance and mortality in idiopathic pulmonary arterial hypertension. Journal of the American College of Cardiology, 47(4), 799-803 (2006).
Naeije, Robert, and Sandrine Huez. "Right ventricular function in pulmonary hypertension: physiological concepts." European heart journal supplements 9.suppl H: H5-H9.(2007).
PCT International Search Report & Written Opinion dated Mar. 24, 2015 for PCT/IB/2015/050066.
PCT International Search Report & Written Opinion dated Mar. 24, 2015 for PCT/IB/2015/050068.
PCT International Search Report dated Mar. 8, 2012 in PCT Patent Application No. PCT/US2011/061815.
Pellegrini, P. et al., Prognostic relevance of pulmonary arterial compliance in patients with chronic heart failure. Chest Journal, 145(5), 1064-1070 (2014).
Procyrion. "A tool for the Cardiologist", published Jul. 3, 2013. http://web.archive.org/web/20130703020540/http://www.procyrion.com/technology.
Reuben, S. R., Compliance of the human pulmonary arterial system in disease. Circulation Research, 29(1), 40-50 (1971).
Saouti, N. et al., The arterial load in pulmonary hypertension. European Respiratory Review, 19(117): 197-203 (2010).
Second Written Opinion dated Jul. 7, 2016 in Int'l PCT Patent Application Serial No. PCT/US2015/036201.
Souza, R. (2008). Assessment of compliance in pulmonary arterial hypertension.
Sunagawa, K., et. al., Left ventricular interaction with arterial load studied in isolated canine ventricle. American Journal of Physiology-Heart and Circulatory Physiology, 245(5), H773-H780 (1983).
Wang, Z., et al., Pulmonary vascular wall stiffness: an important contributor to the increased right ventricular afterload with pulmonary hypertension. Pulmonary circulation, 1(2), 212-223 (2011).
"Aria CV Awarded Top Prize At TCT's 2018 Shark Tank Competition", https://cathlabdigest.com/content/Aria-CV-Awarded-Top-Prize-TCT's-2018-Shark-Tank-Competition, dated Oct. 9, 2018, (accessed Dec. 13, 2019).

(56) References Cited

OTHER PUBLICATIONS

"Aria CV Wins Contest for Pulmonary Arterial Hypertension Medical Device," https://pulmonaryhypertensionnews.com/2018/09/27 /aria-cv-wins-contest-pulmonary-arterial-hypertension-medical-device/, dated Sep. 27, 2018, (accessed Dec. 13, 2019).
"Aria CV Wins top honors in device organization Shark Tank Competition," http://www.startribune.com/loe-carlson/271816721, dated Apr. 22, 2019, (accessed Dec. 13, 2019).
Brian, Jr., M.D., Johnny E., Associate Professor, Department of Anesthesia, University of Iowa College of Medicine, "Gas Exchange, Partial Pressure Gradients, and the Oxygen Window," Oct. 2001.
Extended European Search Report dated Jun. 19, 2019 in EP Patent Appl. Serial No. EP19165162.9, 5 pages.
International Search Report & Written Opinion dated Nov. 27, 2020 in Int'l PCT Patent Appl. Serial No. PCT/US2020/049252.
Lategola, Michael T., Measurement of Total Pressure of Dissolved Gas in Mammalian Tissue In Vivo, J. Appl. Physiol., 19:322-4 (1964).
Loring, Stephen H., et al., Gas Exchange in Body Cavities, Handbook of Physiology—The Respiratory System IV, Chapter 15, pp. 283-295 (1987).
Piiper, Johannes, Physiological Equilibria of Gas Cavities in the Body, Handbook of Physiology. Section 3: Respiration, vol. II, pp. 1205-1218 (1965).
Tenney, et al., Gas Transfers in a Sulfur Hexafluoride Pneumoperitoneum, Journal of Applied Physiology, 6(4):201-208 (1953).
Tucker, et al., Inert Gas Exchange in Subcutaneous Gas Pockets of Air-Breathing Animals: Theory and Measurement, Respiration Physiology, 1:151-171 (1966).
Written Opinion dated Mar. 8, 2012 in International PCT Patent Application Serial No. PCT/US11/061815.
Written Opinion dated Sep. 8, 2011 in International PCT Patent Application Serial No. PCT/US11/038558.

\* cited by examiner

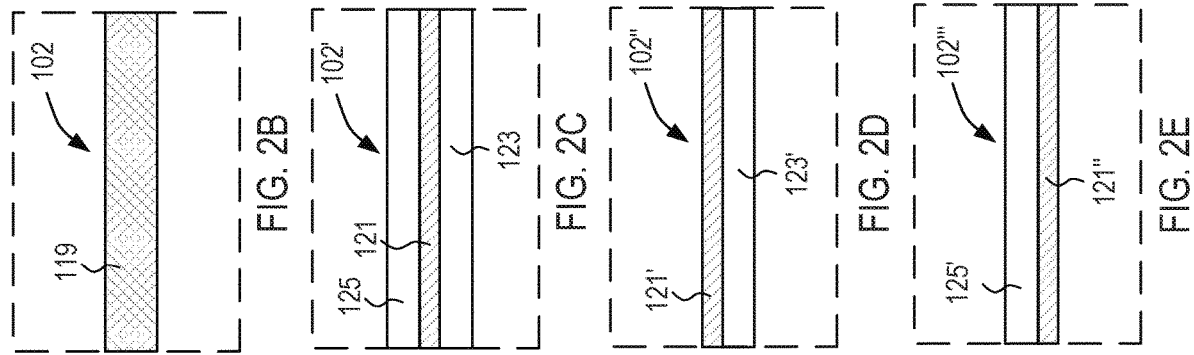
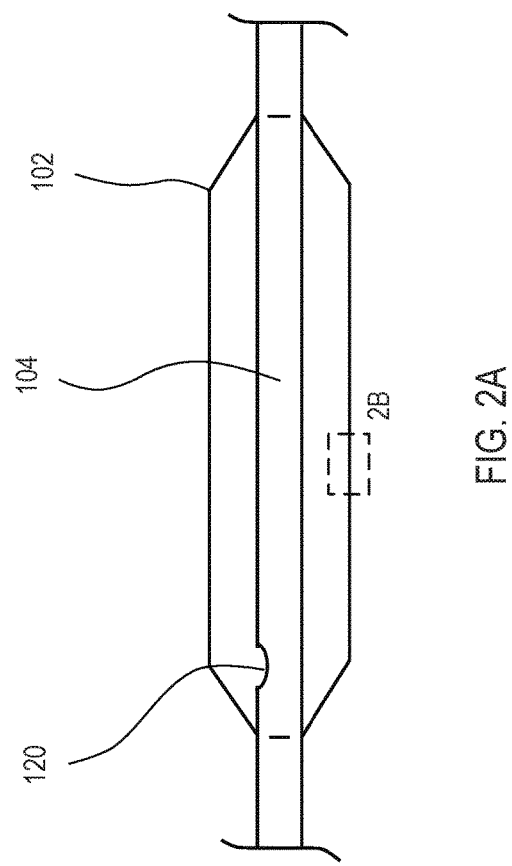

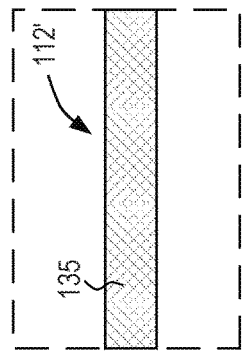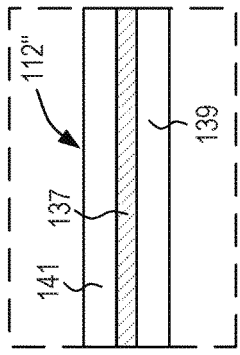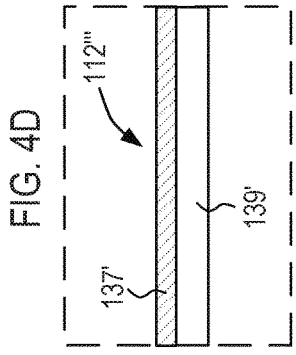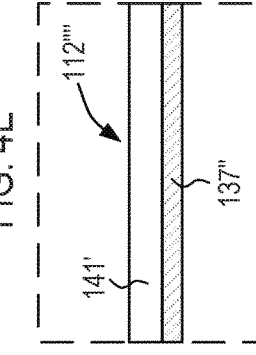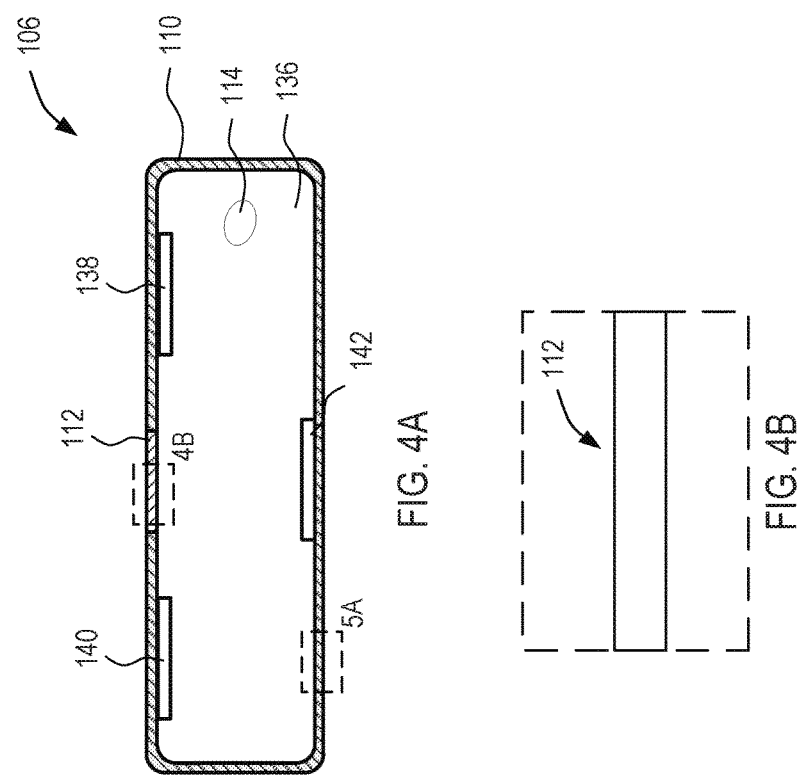

DIFFUSION RESISTANT IMPLANTABLE DEVICES FOR REDUCING PULSATILE PRESSURE

I. TECHNICAL FIELD

This application generally relates to systems and methods for treating pulmonary hypertension, including diffusion-resistant implantable devices for reducing pulsatile load in the pulmonary artery.

II. BACKGROUND

Pulmonary hypertension (PH) is defined as a rise in mean pressure in the main pulmonary artery. PH may arise from many different causes, but, in all patients, has been shown to increase mortality rate. A deadly form of PH arises in the very small branches of the pulmonary arteries and is known as Pulmonary Arterial Hypertension (PAH). In PAH, the cells inside the small arteries multiply due to injury or disease, decreasing the area inside of the artery and thickening the arterial wall. As a result, these small pulmonary arteries narrow and stiffen, causing blood flow to become restricted and upstream pressures to rise. This stiffening, or reduction in compliance, increases the workload on the right ventricle, contributing to right heart failure, the ultimate cause of death in pulmonary hypertension. This increase in stiffness and pressure in the main pulmonary artery is the common connection between all forms of PH regardless of underlying cause.

PH causes the larger pulmonary arteries to dilate and stiffen. As the stiffening progresses, the main pulmonary artery is less able to stretch to accommodate each incoming stroke volume. The lack of expansion causes a much larger rise in pressure with each heartbeat (called systolic or peak pressure) than would occur in a healthy, compliant vessel. In between heartbeats, the arteries in a diseased patient do not recoil as they normally would and diastolic pressure and flow through the lungs drops resulting in a reduction in cardiac output. The heart has to work harder to push the same stroke volume of blood into the stiff artery at a higher pressure. At the same time, the high pulse pressure travels down the pulmonary arteries to the small vessels and activates molecular signaling pathways causing the cells to multiply more rapidly, accelerating disease progression.

As the pressure within the pulmonary artery increases, the right side of the heart enlarges and thickens to compensate, but eventually reaches the point where it cannot continue to pump enough blood through the lungs to satisfy the body's need for oxygenated blood. This progressive reduction of blood flow is first noticed as shortness of breath when exercising. Over time, the right ventricular remodeling worsens and patients lose the ability to maintain a normal daily level of activity and enter end-stage heart failure where the right ventricle dilates and loses its ability to contract, reducing blood flow even further. At the end-stage, the patient mortality rate is high.

Current treatment protocols for PH and Primary PAH include administration of pharmaceuticals. However, such pharmaceuticals are extremely expensive and not sufficiently effective.

Previously known implantable systems having a balloon, conduit, and reservoir have been described. By implanting a balloon having a fluid therein, e.g., a gas that may be compressible, in the pulmonary artery, compliance is restored, and thus the deleterious effects of vessel stiffening are reduced. U.S. Pat. Nos. 9,017,359 and 9,333,328 to Scandurra and U.S. Pat. Nos. 8,876,850, 9,039,725, and 9,242,082 to Vollmers, assigned to the assignee of the present disclosure, the entire disclosure of each of which are incorporated by reference herein, describe exemplary systems and methods.

During right ventricular systole, the increased blood pressure in the pulmonary artery compresses the fluid in a balloon, and forces the fluid out of the balloon through a conduit and into a reservoir, which may be implanted outside of the vascular system. During right ventricular diastole, the drop in blood pressure within the pulmonary artery results in a pressure gradient between the fluid pressure in the reservoir and the deflated balloon in the pulmonary artery. This gradient causes the fluid to flow back through the conduit into the balloon from the reservoir. The effectiveness of the implantable system is influenced by the amount of fluid transferred between the balloon and the reservoir during the cardiac cycle. As such, it is important that the volume of fluid in the closed system be maintained substantially constant for as long as possible, especially for long-term implantable systems. It is also important to minimize diffusion of other non-desirable liquids and vapors through the system surfaces. For example, diffusion of water molecules into the system from the blood may result in the formation of water drops or pools which may impede or restrict the beneficial flow within the system.

As described in U.S. Pat. Nos. 9,017,359 and 9,333,328 to Scandurra and U.S. Pat. Nos. 8,876,850, 9,039,725, and 9,242,082 to Vollmers, assigned to the assignee of the present disclosure, the entire disclosure of each of which are incorporated by reference herein, it is beneficial to use a flexible polymeric balloon to reduce energy loss during cyclic function, allow for high cycle count with low risk of fatigue driven failure, maintain biocompatibility, and allow for tight wrapping and small insertion size required for interventional procedures. Accordingly, selection of a fluid, e.g., a liquid or a gas, that does not readily diffuse through a polymeric balloon membrane may assist in reducing diffusion through the membrane of the balloon. However, there are additional requirements that must be balanced with the reduction in permeability. First, a functional gas preferably diffuses easily into blood so that a failure of the balloon or a system component does not cause a non-soluble gas embolus to occlude blood flow in the vasculature. Additionally, the preferred gas for a system of the type described in the aforementioned patents should have very low viscosity and molecular weight in order to optimize gas flow and minimize turbulence and energy loss. For example, $N_2$ tends to diffuse relatively slowly through most polymer membranes, but $N_2$ does not dissolve into blood well and may be considered a risk for embolism. $CO_2$ is a candidate gas due to the very high solubility of the $CO_2$ in blood, but $CO_2$ is a relatively large gas molecule, which may cause turbulent flow that could hinder device performance. Additionally, preliminary tests on the compatibility of $CO_2$ with many of the commercially available polymer membranes shows high permeability through such membranes. Helium is a candidate gas due to a relatively high solubility in blood and a very low molecular size, which helps to optimize gas flow through the implantable system. Although helium diffuses through polymers fairly readily, it does so at a rate slower than that of $CO_2$.

Another approach to reducing diffusion of a gas through the implantable system involves selecting a material that minimizes gas diffusion. However, a balance must be achieved between the reduction of permeability and the functionality of the device. A preferred balloon would be easily deformable when exposed to the pressures encountered in the pulmonary artery. Because the balloon should survive long-term, e.g., for millions of cycles, trade-offs must be made between rigidity and durability. In particular, energy expended in deforming the polymer of the balloon rather than moving gas through the system is lost as noise, friction, or heat, and cannot be recovered during right ventricular diastole, reducing the energetic efficiency of the device. Additionally, there is a general relation between rigidity and durability according to which a more rigid polymeric balloon is more likely to crease and buckle, ultimately resulting in polymer fatigue and loss of balloon integrity.

Relative permeability rates of known materials and common gases are known, for example, for polyethylene, polyurethane, polyurethane/polycarbonate blends, polyvinylidine fluoride, polyvinylidine chloride, polydimethylsiloxane, butyl, neoprene, nitrile, nylon, silicone, PEEK, and composite blends of many of these materials. In addition, the concept of adding additional materials and layers to existing materials to form composites or multilayer materials is also possible. In some situations, adding a particulate to the polymer to improve the vapor barrier properties of a material has been demonstrated to reduce diffusion of a gas through the material. For example, nanoclay platelets, a material with a large aspect ratio of diameter to thickness, may be compounded into a polymer with these platelets lying flat along the plane of the film. The clay nanoparticle itself is impermeable to gas, so the gas must pass around these platelets to migrate through the film. The passage of gas through a vapor barrier containing layers of these nanoclay platelets is greatly impeded due to the tortuous path that the gas must follow to navigate, resulting in a much slower gas transfer rate than that of the base polymer. While some reduction in gas diffusion has been observed through material selection, it would be desirable to have materials with reduced diffusion to a level suitable for use in a clinical device intended for long-term implantation, e.g., a period of several weeks to years. Such materials would reduce the frequency of periodic fluid refills in the implantable long-term system through a subcutaneous port which may be inconvenient for the patient.

It would be desirable to provide systems and methods for treating heart disease, such as pulmonary hypertension and right heart failure, where the period between refilling the fluid may be extended as long as possible to provide patient convenience and safety, as well as device efficacy.

It further would be desirable to provide systems and methods for treating heart disease having a material(s) selected to effectively reduce or eliminate diffusion of the internal fluid out of, and external fluid into, the implantable system, in addition to selecting a fluid that does not readily diffuse through the material.

III. SUMMARY

The present disclosure overcomes the drawbacks of previously-known systems by providing diffusion-resistant systems and methods for treating heart disease, e.g., pulmonary hypertension and/or right heart failure. The diffusion-resistant system may include a reservoir that holds a fluid, e.g., a compressible or non-compressible fluid, therein, a transvascular conduit having a distal region and a proximal region coupled to the reservoir, and a compliant body adapted to be implanted in a vessel, e.g., a pulmonary artery, and coupled to the distal region of the transvascular conduit. The compliant body may contract during systole to move the fluid towards the reservoir and expand during diastole to thereby reduce peak pressure in the vessel. In accordance with one aspect of the present invention, the compliant body preferably is formed from a carbon-polymer composite configured to resist diffusion of the fluid through the compliant body while the compliant body remains implanted in the vessel, e.g., for implantation in the vessel for a period of several weeks to years.

The compliant body may be formed from a carbon-polymer composite made of at least one of a graphene oxide, a reduced graphene oxide, a graphene nanoribbon, a carbon nanotube, a buckminsterfullerene, graphene nanosheets, graphene nanoflakes, graphene nanoplatelets, in multi-layer or single layer forms of the aforementioned, or any one of these modified by chemical or physical processing or by the addition or removal of functional groups. The carbon-polymer composite may be a graphene-polymer matrix having graphene compounded into a polymer, dispersed in a polymer solution, or a graphene sandwiched between two or more layers of material including polymers. In one embodiment, the carbon-polymer composite may be a graphene configured to be deposited onto the inner and/or outer layer of the compliant body. For example, the graphene may be deposited by at least one of dip coating, spraying, rolling, powder coating, solvent interface trapping, solvent interface dipping, hydro dipping, solution dipping, or in situ formation. As such, the deposited graphene may be graphene in a vapor form, graphene alone, graphene in a liquid suspension, or graphene in a solid suspension with or without additional suspension components. In addition, the conduit, and the septum and housing of the reservoir may also be made of a carbon-polymer composite to resist diffusion of the fluid through the conduit and/or the septum and housing of the reservoir. Graphene may also be formed in situ on the surface of the implant from elemental carbon atoms or other precursors. Graphene may be deposited on a balloon mold or mandrel prior to forming the balloon so the act of fabricating the balloon incorporates the preformed graphene layer.

The diffusion-resistant system also may have an anchor for securing the compliant body within the vessel. The anchor may be coupled to the conduit proximal and/or distal to the compliant body.

IV. BRIEF DESCRIPTION OF THE DRAWINGS

FIG. 2A shows a cross-sectional view along line 2A in FIG. 1 of an exemplary compliant body.

FIGS. 2B through 2E show a magnified view of box 2B in FIG. 2A for various embodiments of the compliant body membrane.

FIG. 4A shows a cross-sectional view along line 4A in FIG. 1 of an exemplary reservoir.

FIGS. 4B through 4F show a magnified view of box 4B in FIG. 4A for various embodiments of the septum of the reservoir.

V. DETAILED DESCRIPTION

Systems and methods of the present disclosure include diffusion-resistant implantable devices for restoring compliance to a portion of a patient's vasculature, such as the pulmonary system. In accordance with the principles of the present disclosure, the systems may be optimized for use in treating all forms of pulmonary hypertension (PH) as described in the World Health Organization Clinical Classification, including Pulmonary Arterial Hypertension (PAH), and right heart failure (RHF).

Figure 1:
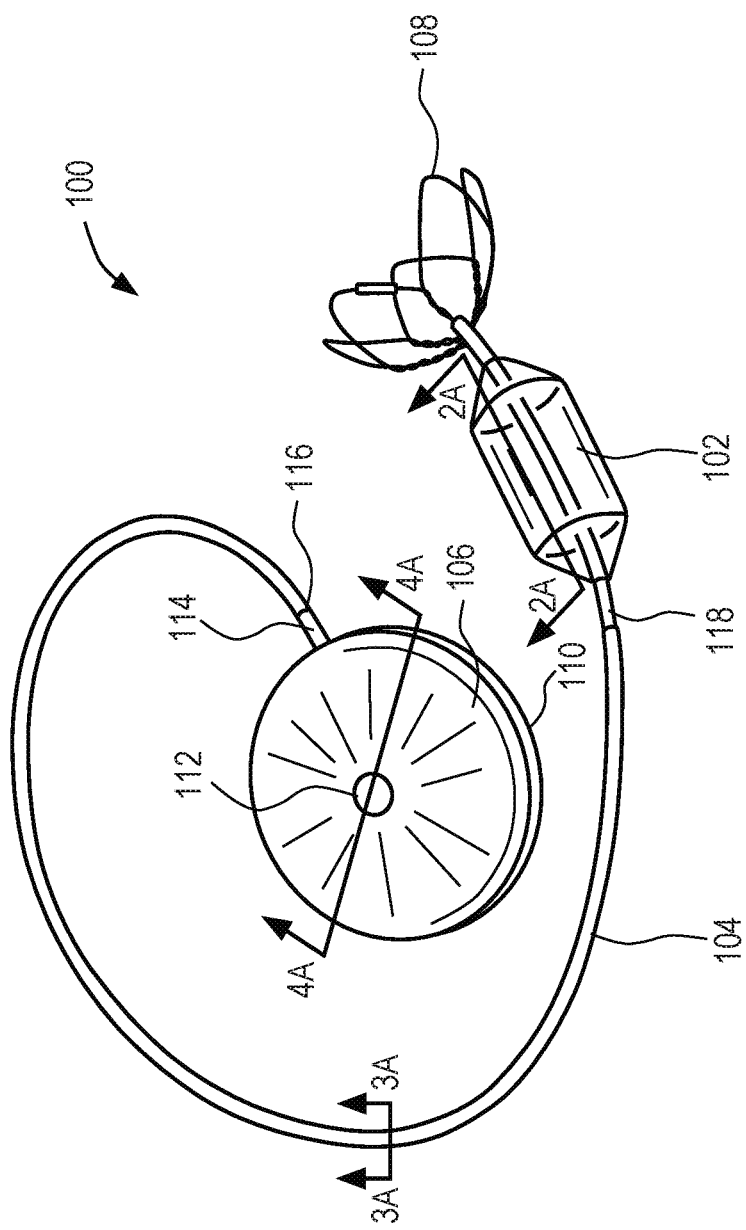
FIG. 1 shows an exemplary embodiment of a system constructed in accordance with the principles of the present disclosure.

Referring to FIG. 1, an overview of an exemplary system conducted in accordance with the principles of the present disclosure is provided. System 100 may include compliant body 102, conduit 104, and reservoir 106. Compliant body 102 is adapted to be implanted in a body lumen, e.g., the pulmonary artery which includes the main pulmonary artery and the pulmonary artery branches. Preferably, compliant body 102 is configured for long-term implantation within the body lumen, e.g., from a period of several weeks, months or years. With each heartbeat, fluid within system 100 moves towards or away from compliant body 102. By contracting and getting smaller in volume, compliant body 102 mimics the expansion of the vessel (increasing intravascular volume) that naturally occurs in a healthy person, making room for incoming blood. This contracting action has the effect of absorbing or reducing the peak systolic pressure and also reducing the rate of change (e.g., acceleration) of blood flow. When the heart begins to relax, the pulmonary valve closes and the pressure in the main pulmonary artery begins to drop. As the pressure drops below the pressure level in reservoir 106, fluid flows from reservoir 106 to compliant body 102 such that the potential energy within compliant body 102 increases. During diastole, compliant body 102 preferably expands to about the full volume of compliant body 102 to increase pressure in the pulmonary artery to push additional blood through the artery towards the lungs, thereby increasing cardiac output. Continuous expansion and contraction of compliant body 102 is expected to reduce peak systolic pressure and increase diastolic pressure, thus reducing the load on the right ventricle and increasing heart efficiency. Preferably compliant body 102 is designed to handle multiple expansion and contraction cycles over the course of long-term implantation, e.g., over a period of weeks, months or years.

As will be appreciated by those of ordinary skill in the art, any suitable biocompatible fluid, e.g., liquid or gas, may be used in the system 100. The fluid may be a compressible gas such that the volume of the gas changes in response to a change in pressure in the artery (or other implantation location of compliant body 102) consistent with the gas bulk modulus of the gas. Furthermore, the gas is preferably nontoxic, easily absorbed by the body, and has physical properties that resist diffusion through the wall of the compliant body. Suitable gases may include, but are not limited to, nitrogen, carbon dioxide, argon, neon, and helium. Optionally, the gas may have therapeutic properties, such as nitric oxide which causes vasodilation.

Referring now to FIG. 2A, a cross-sectional view of an exemplary compliant body of system 100 along line 2A-2A in FIG. 1 is provided. As shown in FIG. 2A, conduit 104 may extend through and past compliant body 102 and includes one or more ports 120 in the portion of conduit 104 within compliant body 102 to permit fluid to be introduced from conduit 104 into the interior space of compliant body 102. Compliant body 102 has a maximum diameter, a length, and a wall/membrane thickness. Preferably, compliant body 102 has a maximum diameter between about 1.5-3.5 cm, and preferably about 2.5 cm; a length between about 3-8 cm, and preferably about 5-6 cm; and a wall/membrane thickness between about 0.001-0.020 inches. Compliant body 102 preferably has a diameter in the fully expanded state that is less than the diameter of the pulmonary artery. For example, the diameter of compliant body 102 in the fully expanded state may be between about 20-90%, and more preferably about 50-70%, of the diameter of the pulmonary artery in the area at which compliant body 102 is implanted. Applicant has discovered that utilizing a compliant body sized such that the ratio of the inner diameter of the body lumen to the maximum balloon diameter is below a predetermined threshold, e.g., from about 0.9 to about 0.6, maintains pressure upstream from the compliant body at a level substantially similar to pressure downstream from the compliant body, thereby regulating pressure drop across the compliant body during the cardiac cycle. Compliant body 102 is preferably sized with a maximum diameter that will not obstruct blood flow or increase resistance to flow in the pulmonary artery.

The surface of compliant body 102 may be biomimetic, have antithrombotic properties, and/or the external surface compliant body 102 may be coated with a material to prevent thrombus formation, such as heparin or the like. Additionally or alternatively, the surface of compliant body 102 may be lubricious, such that it impedes adhesion of body components such as platelets, proteins, endothelium, endocardium, or heart valves. Additionally or alternatively, the compliant body material or the surface of compliant body 102 may be composed of a material that minimizes chemical or oxidative degradation. Any suitable biocompatible lubricant may be used including, but not limited to, silicone or hyaluronan based materials. The shape of compliant body 102 may also be carefully defined to eliminate dead space in the surrounding blood flow to minimize thrombus formation.

Referring now to FIGS. 2B through 2E, various embodiments of the material(s) of compliant body 102 are provided. Compliant body 102 is preferably a compliant or semi-compliant balloon and may be formed from one or more materials that resist diffusion of internal fluid out of the system and of external fluid into the system, e.g., a carbon-polymer composite such as a graphene-polymer matrix having graphene compounded into a polymer, dispersed in a polymer solution, or a graphene sandwiched between two layers of polymer. Graphene is a thin layer of pure carbon and more specifically, a single tightly-packed layer of carbon atoms that form a hexagonal honeycomb lattice. A single layer of graphene is one atom thick, completely impervious to helium diffusion, and highly resistant to most other gases. It may be used as single layer or multi-layer material. Small particles of graphene may take a number of forms, for example, graphene platelets. Graphene platelets may be added to a polymer to reduce diffusion to a level exceeding other materials. One preferred form of graphene that may be used as a vapor barrier is graphene nanoribbons (GNR). GNR may be synthesized in a number of ways, one of which is slitting or "unzipping" a carbon nanotube. GNR may be added to a polymer to reduce gas transmission. For example, GNR and polymers may be combined with as little as 0.5% by weight GNR to reduce gas transmission by as much as three orders of magnitude. Other forms of graphene that may be used include a graphene oxide and/or a reduced graphene oxide. Alternatively, the carbon-polymer composite with improved resistance to gas permeability may be formed from other forms of carbon, e.g., a carbon nanotube, a buckminsterfullerene, or any of the graphene forms previously described. The polymer may include, for example, polyethylene, polyurethane, polyurethane/polycarbonate blends, polyvinylidine fluoride, butyl, neoprene, nitrile, nylon, silicone, PEEK, polyvinylidine chloride, polydimethylsiloxane, or any combination thereof.

The wall of compliant body 102 may include a carbon-polymer composite material made of a single layer of a graphene-polymer matrix or multiple layers of multiple materials with one or more layers including graphene. For example, as shown in FIG. 2B, the wall of compliant body 102 may be formed of a carbon-polymer composite made of a single layer of graphene-polymer matrix 119. Graphene-polymer matrix 119 is preferably made of graphene compounded into a polymer. The wall of compliant body 102 formed of graphene-polymer matrix 119 is configured to reduce diffusion of fluid through graphene-polymer matrix 119 and thereby through the wall of compliant body 102.

Referring now to FIG. 2C, an alternative embodiment of the wall of compliant body 102 is described. In FIG. 2C, the wall of compliant body 102' may be formed of a carbon-polymer composite made of graphene layer 121 sandwiched between outer layer polymer 125 on the outer surface of compliant body 102', and inner layer polymer 123 on the inner surface of compliant body 102' facing the inner cavity of compliant body 102'. The wall of compliant body 102' formed of graphene layer 121 sandwiched between outer layer polymer 125 and inner layer polymer 123 is configured to reduce diffusion of fluid through graphene layer 121, outer layer polymer 125, and inner layer polymer 123 and thereby through the wall of compliant body 102'.

Referring now to FIGS. 2D and 2E, alternative embodiments of the material(s) of compliant body 102' are described. Compliant body 102" and compliant body 102'" are constructed similarly to compliant body 102' of FIG. 2C, wherein like components are identified by like-primed reference numbers. Thus, for example, graphene layer 121' in FIG. 2D and graphene layer 121" in FIG. 2E correspond to graphene layer 121 of FIG. 2C, etc. As will be observed by comparing FIG. 2D with FIG. 2C, the carbon-polymer composite may be made of inner layer polymer 123' having graphene layer 121' deposited on the outer surface of compliant body 102" disposed within the body lumen. For example, graphene layer 121' may be deposited on the outer surface of compliant body 102" by at least one of dip coating, spraying, rolling, solvent interface trapping, solvent interface dipping, hydro dipping, solution dipping, or powder coating. As such, the deposited graphene may be, for example, graphene alone, graphene in a liquid suspension, or graphene in a solid suspension. The wall of compliant body 102" formed of graphene layer 121' deposited on inner layer polymer 123' is configured to reduce diffusion of fluid through graphene layer 121' and inner layer polymer 123' and thereby through the wall of compliant body 102".

Alternatively, as depicted in FIG. 2E, the carbon-polymer composite may be made of outer layer polymer 125' having graphene layer 121" deposited on the inner surface of compliant body 102'" facing the inner cavity of compliant body 102'". Similarly, graphene layer 121" may be deposited on the inner surface of compliant body 102'" by, for example, at least one of dip coating, spraying, rolling, or powder coating. The wall of compliant body 102'" formed of graphene layer 121" deposited on outer layer polymer 125' is configured to reduce diffusion of fluid through graphene layer 121" and outer layer polymer 125' and thereby through the wall of compliant body 102'".

Referring back to FIG. 1, compliant body 102 may be secured within the body lumen via anchor 108. Anchor 108 may be coupled to compliant body 102, to conduit 104 proximal to compliant body 102, and/or to conduit 104 distal to compliant body 102 as illustrated. Preferably, anchor 108 is configured to expand from a contracted state, e.g., when compressed in a sheath, to an expanded state responsive to an event, e.g., exposure from the sheath or expansion of compliant body 102. In the expanded state, anchor 108 is sized to contact the inner wall of the body lumen or another anchor deployed within the body lumen.

Conduit 104 is configured to couple compliant body 102 to reservoir 106. Conduit 104 includes proximal region 116 and distal region 118. In the illustrated embodiment, conduit 104 is coupled to port 114 of reservoir 106 at proximal region 116 and coupled to compliant body 102 at distal region 118. Preferably, conduit 104 has a length suitable to extend from reservoir 106 in the subcutaneous space, through the subclavian vein, and past the pulmonary valve to compliant body 102 implanted within the pulmonary artery. Preferably, conduit 104 extends through and past compliant body 102 a predetermined distance and includes one or more ports in the portion of conduit 104 within compliant body 102 to permit fluid to be introduced from conduit 104 into the interior space of compliant body 102. In one embodiment, conduit 104 has a length between about 20-100 cm, and more preferably about 60 cm. The diameter of conduit 104 is preferably about 3-5 mm or about 4 mm at distal region and may be variable along the length of conduit 104 up to a predetermined maximum diameter, e.g., about 15 mm. Preferably, conduit 104 has a wall/membrane thickness between about 0.005 to 0.020 inches.

As described above, at least a portion of conduit 104 may extend through and past compliant body 102. As such, the surface of the conduit 104 within compliant body 102 may be coated with compliant material or porous compliant material which acts to cushion the surface of the conduit. Suitable materials may include polymers, open cell foamed rubber, foamed rubber, silicones, woven or knitted fibers, dense brush-type materials such as Velcro, and the like. Such coatings will prevent acoustic pressure spikes in the surrounding blood when the compliant body collapses completely.

Figure 3F:
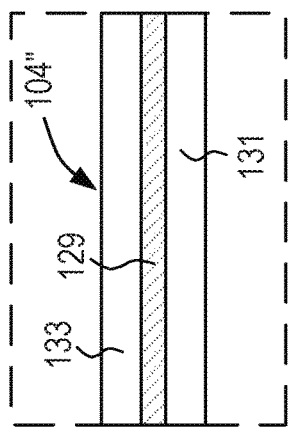
FIGS. 3D through 3H show a magnified view of box 3D in FIG. 3A for various embodiments of the conduit membrane.
Figure 3G:
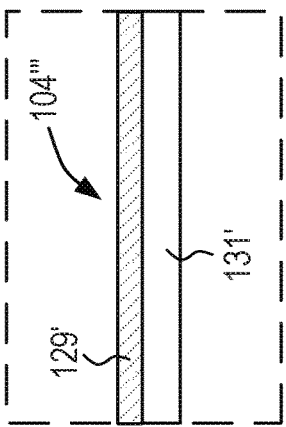
Figure 3H:
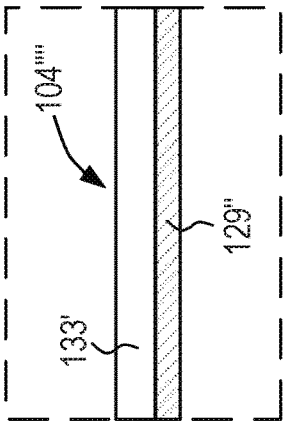
Figure 3D:
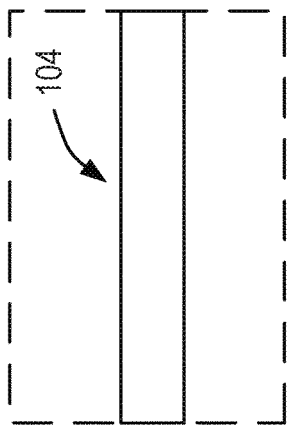
Figure 3E:
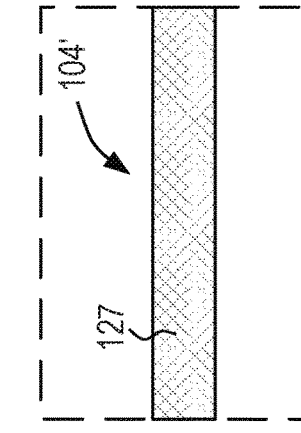
Figure 3A:
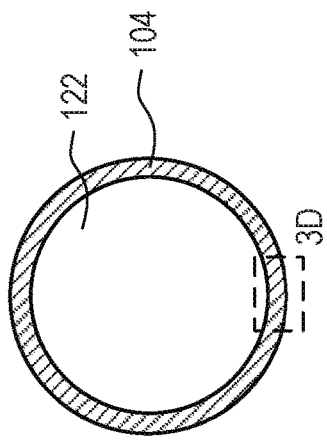
FIG. 3A shows a cross-sectional view along line 3A in FIG. 1 of an exemplary conduit.
Figure 3B:
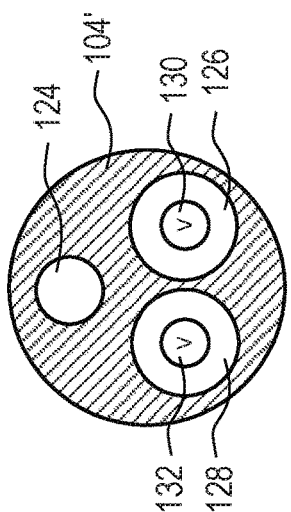
FIGS. 3B and 3C show cross-sectional views along line 3A in FIG. 1 for alternative conduits.
Figure 3C:
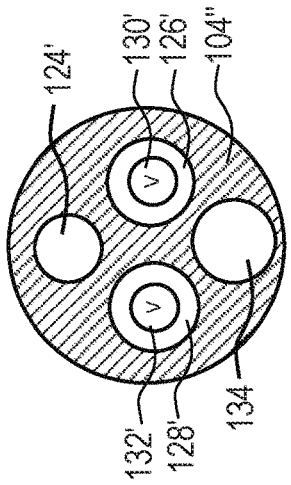

Referring now to FIGS. 3A, 3B, and 3C, cross-sectional views of alternative conduits taken along line 3A-3A in FIG. 1 are shown, wherein the number of lumens within the conduits vary. In FIG. 3A, conduit 104 has lumen 122. Lumen 122 is configured to permit fluid to move back and forth between compliant body 102 and reservoir 106. Lumen 122 preferably extends from proximal region 116 to a port within compliant body 102. Conduit 104 also may include a second lumen (not illustrated) sized to permit a guidewire and/or a balloon retrieval device to be advanced therethrough that preferably extends from the proximal end of conduit 104 out the distal end of conduit 104 past compliant body 102.

In FIG. 3B, conduit 104' is constructed similarly to conduit 104 of FIG. 3A, wherein like components are identified by like-primed reference numbers. As will be observed by comparing FIGS. 3A and 3B, conduit 104' includes three lumens; guidewire lumen 124, inflow lumen 126, and outflow lumen 128. Guidewire lumen 124 is sized to permit a guidewire and/or a balloon retrieval device to be advanced therethrough and preferably extends from the proximal end of conduit 104 out the distal end of conduit 104 past compliant body 102. Inflow lumen 126 is configured to permit fluid to move only from reservoir 106 to compliant body 102, e.g., using one-way valve 130. Inflow lumen 126 preferably extends from proximal region 116 to a port within compliant body 102. Outflow lumen 128 is configured to permit fluid to move only from compliant body 102 to reservoir 106, e.g., using one-way valve 132 disposed in an opposite direction to valve 130. Outflow lumen 128 preferably extends from proximal region 116 to a port within compliant body 102.

In FIG. 3C, conduit 104" is constructed similarly to conduit 104' of FIG. 3B, wherein like components are identified by like-primed reference numbers. As will be observed by comparing FIGS. 3B and 3C, conduit 104" includes a fourth lumen: lumen 134. Lumen 134 is configured to permit a balloon retrieval device to be advanced therethrough and has a diameter larger than guidewire lumen 124'.

Referring now to FIG. 3D, the wall of conduit 104 may include a single layer of polymer or any other suitable material commonly used for long-term implantable transvascular conduits. Alternatively, the wall of conduit 104 may include diffusion-resistant material such as a single layer of a graphene-polymer matrix or multiple layers of multiple materials with one or more layers including graphene such that conduit 104 is diffusion-resistant. For example, as depicted in FIG. 3E, the wall of conduit 104' may include a carbon-polymer composite made of a single layer of graphene-polymer matrix 127 made of graphene compounded into a polymer. The wall of conduit 104' formed of graphene-polymer matrix 127 is configured to reduce diffusion of fluid through graphene-polymer matrix 127 and thereby through the wall of conduit 104'. Additionally, any of the aforementioned conduit walls may have other features to improve the performance of the system. For example, metallic or polymeric coils or braid may be embedded within the walls of the conduit to reduce the likelihood of conduit kinking, or the outside of the conduit may be coated to prevent thrombus formation or to reduce catheter insertion forces.

An alternative embodiment of the material(s) of conduit 104 is depicted in FIG. 3F, in which the wall of conduit 104" may be formed of a carbon-polymer composite made of graphene layer 129 sandwiched between outer layer polymer 133 on the outer surface of conduit 104", and inner layer polymer 131 on the inner surface of conduit 104" facing the inner cavity of conduit 104". The wall of conduit 104" formed of graphene layer 129 sandwiched between outer layer polymer 133 and inner layer polymer 131 is configured to reduce diffusion of fluid through graphene layer 129, outer layer polymer 133, and inner layer polymer 131 and thereby through the wall of conduit 104".

Referring now to FIGS. 3G and 3H, alternative embodiments of the material(s) of conduit 104' are described. Conduit 104''' and conduit 104'''' are constructed similarly to conduit 104" of FIG. 3F, wherein like components are identified by like-primed reference numbers. Thus, for example, graphene layer 129' in FIG. 3G and graphene layer 129" in FIG. 3H correspond to graphene layer 129 of FIG. 3F, etc. As will be observed by comparing FIG. 3G with FIG. 3F, the carbon-polymer composite may be made of inner layer polymer 131' having graphene layer 129' deposited on the outer surface of conduit 104''' disposed within the body lumen. For example, graphene layer 129' may be deposited on the outer surface of conduit 104''' by, e.g., dip coating, spraying, brushing, rolling, solvent interface trapping, solvent interface dipping, hydro dipping, solution dipping, powder coating, vapor deposition, etc. As such, the deposited graphene may be, for example, graphene alone, graphene in a liquid suspension, or graphene in a solid suspension. The wall of conduit 104''' formed of graphene layer 129' deposited on inner layer polymer 131' is configured to reduce diffusion of fluid through graphene layer 129' and inner layer polymer 131' and thereby through the wall of conduit 104'''.

Alternatively, as depicted in FIG. 3H, the carbon-polymer composite may be made of outer layer polymer 133' having graphene layer 129" deposited on the inner surface of conduit 104'''' facing the inner cavity of conduit 104''''. Similarly, graphene layer 129" may be deposited on the inner surface of conduit 104'''' by, for example, at least one of dip coating, spraying, rolling, solvent interface trapping, solvent interface dipping, hydro dipping, solution dipping, or powder coating. The wall of conduit 104'''' formed of graphene layer 129" deposited on outer layer polymer 133' is configured to reduce diffusion of fluid through graphene layer 129" and outer layer polymer 133' and thereby through the wall of conduit 104''''.

Referring back to FIG. 1, reservoir 106 is configured to receive and hold a fluid, e.g., liquid or gas, therein. Reservoir 106 includes housing 110, septum 112, and port 114. Reservoir 106 may be formed from any suitable material and may include materials that reduce diffusion of fluid from the internal cavity of reservoir 106 out of the system and of external fluid into the system, e.g., a carbon-polymer composite. Preferably, housing 110 is sealed such that when the conduit is attached, no gas or fluid can enter or exit the reservoir except through the conduit itself, and may comprise titanium or other biocompatible material. Reservoir 106 is configured to be implanted subcutaneously in a suitable body cavity, e.g., within a subcutaneous space in a region near the right or left subclavian vein. Reservoir 106 may be free floating within a pocket in the tissue or may be fastened in place with sutures. Although any suitable shape may be used, in one exemplary embodiment, reservoir 106 has a flattened disk shape with rounded edges to reduce irritation to surrounding body tissues. The interior cavity of reservoir 106 is in fluidic communication with the interior cavity of compliant body 102, e.g., via one or more lumens of conduit 104, such that fluid may move between the cavities and/or pressure may equalize between the cavities. Preferably, the interior cavity of reservoir 106 has a volume of about 50-450 ml, and more preferably about 100-250 ml. Optionally, the external surface of reservoir 106 may be lubricious, such that it impedes adhesion of body components such as platelets or proteins. Exemplary but not limiting lubricants may include silicone or hyaluronan based materials.

Septum 112 is constructed to allow the addition of fluid to or the removal of fluid from reservoir 106 using a suitable needle. Septum 112 preferably is implanted subcutaneously to permit transcutaneous needle access to the interior cavity of reservoir 106 through septum 112. Septum 112 is configured to permit repeated needle penetrations while maintaining a fluid-tight seal and may be formed from any suitable material including materials that reduces diffusion of fluid through reservoir 106, e.g., a carbon-polymer composite as described in further detail below. Radiopaque, magnetic, acoustic, or other markers may also be incorporated into or attached to septum 112 to allow for locating, viewing or tracking of septum 112 with a suitable imaging or sensing system.

Port 114 of reservoir 106 is configured to permit fluidic communication between conduit 104 and the interior cavity of reservoir 106. Port 114 may include a suitable structure to permit coupling between conduit 104 and reservoir 106 such as a nipple (as illustrated), threads, ribs, collet or the like.

Referring now to FIG. 4A, a cross-sectional view of an exemplary reservoir of system 100 along line 4A-4A in FIG. 1 is provided. Interior cavity 136 of reservoir 106 may have sensor 138, sensor 140, and getter 142. Sensors 138, 140 are configured to sense one or more parameters of system 100 such as pressure and/or volume within reservoir 106. Such parameters may be used to assist in removing fluid or introducing fluid to achieve the optimal internal pressure or to confirm proper functioning of system 100. Additional parameters that may be sensed within reservoir 106 include temperature, humidity, fluid flow rate, gas or liquid concentration such as $CO_2$ concentration, and pH. Sensors 138 and 140 may include an inductive coil and may be configured to be powered by an external inductive coil, e.g., coil within an external monitoring system similar to the external monitoring system described in U.S. Pat. No. 8,876,850 to Vollmers, assigned to the assignee of the present disclosure, the entire disclosure of which is incorporated by reference herein. In such an embodiment, sensors 138, 140 may remain off or in a standby mode until receipt of power; after which sensors 138, 140 sense one or more parameters and transmit one or more signals indicative of the sensed parameters externally, e.g., to an external monitoring system, via respective inductive coils. In a preferred embodiment, sensor 138 is a pressure sensor configured to measure pressure within reservoir 106. Measured pressure may be displayed and analyzed externally.

Getter 142 is configured to absorb moisture within reservoir 106. Unwanted moisture from within the body may enter system 100 after implantation. Preferably when the fluid is a gas, getter 142 is configured to absorb liquids within reservoir 106. Getter 142 may be removed and replaced with another getter while system 100 is implanted, after a period of time.

Referring now to FIG. 4B, septum 112 of reservoir 106 may be formed from a single layer of polymer or any other suitable material that may permit repeated needle penetrations while maintaining a fluid-tight seal. Alternatively, septum 112 of reservoir 106 may include diffusion-resistant material such as a single layer of a graphene-polymer matrix or multiple layers of multiple materials with one or more layers including graphene such that septum 112 is diffusion-resistant. For example, as shown in FIG. 4C, septum 112' may include a carbon-polymer composite made of a single layer of graphene-polymer matrix 135 made of graphene compounded into a polymer. Septum 112' formed of graphene-polymer matrix 135 is configured to reduce diffusion of fluid through graphene-polymer matrix 135 and thereby through septum 112'.

Referring now to FIG. 4D, an alternative embodiment of the material(s) of septum 112 is described. In FIG. 4D, septum 112" may be formed of a carbon-polymer composite made of graphene layer 137 sandwiched between outer layer polymer 141 on the outer surface of septum 112", and inner layer polymer 139 on the inner surface of septum 112" facing the inner cavity of the reservoir. The wall of septum 112" formed of graphene layer 137 sandwiched between outer layer polymer 141 and inner layer polymer 139 is configured to reduce diffusion of fluid through graphene layer 137, outer layer polymer 141, and inner layer polymer 139 and thereby through septum 112".

Referring now to FIGS. 4E and 4F, alternative embodiments of septum 112' are described. Septum 112'" and septum 112"" are constructed similarly to septum 112" of FIG. 4D, wherein like components are identified by like-primed reference numbers. Thus, for example, graphene layer 137' in FIG. 4E and graphene layer 137" in FIG. 4F correspond to graphene layer 137 of FIG. 4D, etc. As will be observed by comparing FIG. 4E with FIG. 4D, the carbon-polymer composite may be made of inner layer polymer 139' having graphene layer 137' deposited on the outer surface of septum 112'" disposed within the subcutaneous space of the body. For example, graphene layer 137' may be deposited on the outer surface of septum 112'" by at least one of dip coating, spraying, rolling, solvent interface trapping, solvent interface dipping, hydro dipping, solution dipping, or powder coating. As such, the deposited graphene may be, for example, graphene alone, graphene in a liquid suspension, or graphene in a solid suspension. Septum 112'" formed of graphene layer 137' deposited on inner layer polymer 139' is configured to reduce diffusion of fluid through graphene layer 137' and inner layer polymer 139' and thereby through the wall of septum 112'".

Alternatively, as shown in FIG. 4F, the carbon-polymer composite may be made of outer layer polymer 141' having a graphene layer 137" deposited on the inner surface of septum 112"" facing the inner cavity of the reservoir. Similarly, graphene layer 137" may be deposited on the inner surface of septum 112"" by, for example, at least one of dip coating, spraying, rolling, solvent interface trapping, solvent interface dipping, hydro dipping, solution dipping, or powder coating. Septum 112"" formed of graphene layer 137" deposited on outer layer polymer 141' is configured to reduce diffusion of fluid through graphene layer 137" and outer layer polymer 141' and thereby through the wall of septum 112"".

Figure 5C:
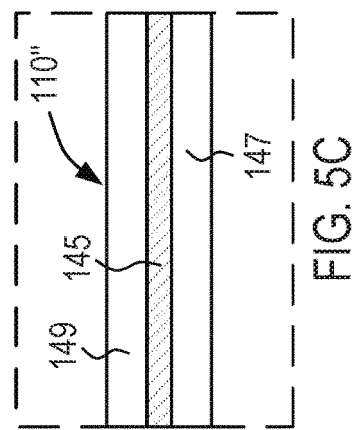
FIGS. 5A through 5E show a magnified view of box 5A in FIG. 4A for various embodiments of the housing of the reservoir.
Figure 5D:
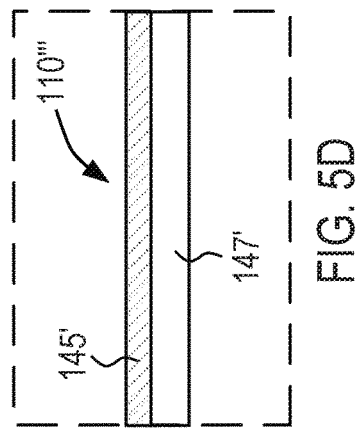
Figure 5E:
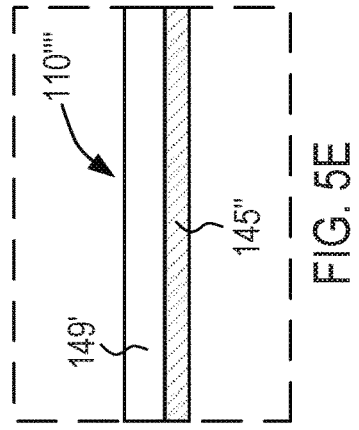
Figure 5A:
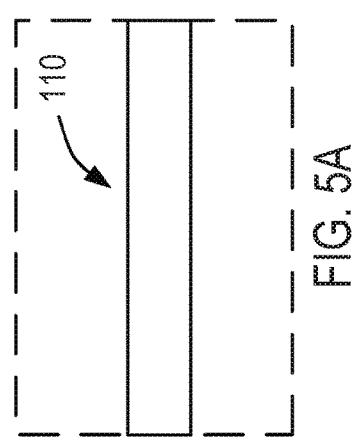
Figure 5B:
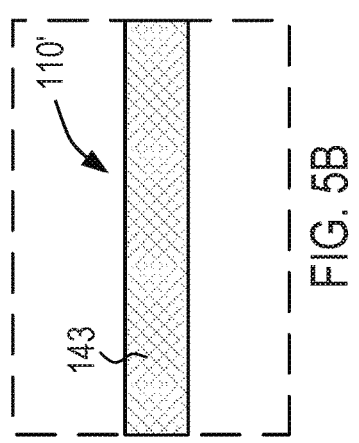

Referring now to FIG. 5A, housing 110 of reservoir 106 may be formed from a single layer of metal, polymer, or any other suitable material that form a diffusion resistant layer. Alternatively, housing 110 of reservoir 106 may include diffusion-resistant material such as a single layer of a graphene-polymer matrix or multiple layers of multiple materials with one or more layers including graphene such that housing 110 is diffusion-resistant. For example, as shown in FIG. 5B, housing 110' may include a carbon-polymer composite made of a single layer of graphene-polymer matrix 143 made of graphene compounded into a polymer. Housing 110' formed of graphene-polymer matrix 143 is configured to reduce diffusion of fluid through graphene-polymer matrix 143 and thereby through housing 110'.

Referring now to FIG. 5C, an alternative embodiment of the material(s) of housing 110 is described. In FIG. 5C, housing 110" may be formed of a carbon-polymer composite made of graphene layer 145 sandwiched between polymer or metal outer layer 149 on the outer surface of housing 110", and polymer or metal inner layer 147 on the inner surface of housing 110" facing the inner cavity of the reservoir. The wall of housing 110" formed of graphene layer 145 sandwiched between outer layer 149 and inner layer 147 is configured to reduce diffusion of fluid through graphene layer 145, outer layer 149, and inner layer 147 and thereby through housing 110".

Referring now to FIGS. 5D and 5E, alternative embodiments of housing 110' are described. Housing 110'" and housing 110'''' are constructed similarly to housing 110'' of FIG. 5C, wherein like components are identified by like-primed reference numbers. Thus, for example, graphene layer 145' in FIG. 5D and graphene layer 145'' in FIG. 5E correspond to graphene layer 145 of FIG. 5C, etc. As will be observed by comparing FIG. 5D with FIG. 5C, the carbon-polymer composite may be made of polymer or metal inner layer 147' having graphene layer 145' deposited on the outer surface of housing 110''' disposed within the subcutaneous space of the body. For example, graphene layer 145' may be deposited on the outer surface of housing 110''' by at least one of dip coating, spraying, rolling, solvent interface trapping, solvent interface dipping, hydro dipping, solution dipping, or powder coating. As such, the deposited graphene may be, for example, graphene alone, graphene in a liquid suspension, or graphene in a solid suspension. Housing 110''' formed of graphene layer 145' deposited on inner layer 147' is configured to reduce diffusion of fluid through graphene layer 145' and inner layer 147' and thereby through the wall of housing 110'''.

Alternatively, as shown in FIG. 5E, the carbon-polymer composite may be made of polymer or metal outer layer 149' having a graphene layer 145'' deposited on the inner surface of housing 110'''' facing the inner cavity of the reservoir. Similarly, graphene layer 145'' may be deposited on the inner surface of housing 110'''' by, for example, at least one of dip coating, spraying, rolling, solvent interface trapping, solvent interface dipping, hydro dipping, solution dipping, or powder coating. Housing 110'''' formed of graphene layer 145'' deposited on outer layer 149' is configured to reduce diffusion of fluid through graphene layer 145'' and outer layer 149' and thereby through the wall of housing 110''''.

As will be understood by one of ordinary skill in the art, septum 112 of the reservoir alone may be formed from one or more materials that resist diffusion of fluid, e.g., a carbon-polymer composite. Alternatively or additionally, as described above, housing 110 may include a diffusion-resistant carbon-polymer composite in accordance with the principles of the present disclosure to reduce or eliminate the diffusion of fluid through the reservoir. As will also be understood by one of ordinary skill in the art, other components of system 100, e.g., reservoir, connectors, seals, and joints, may be made of a diffusion-resistant carbon-polymer composite in accordance with the principles of the present disclosure to reduce or eliminate the diffusion of fluid through system 100.

Figure 6B:
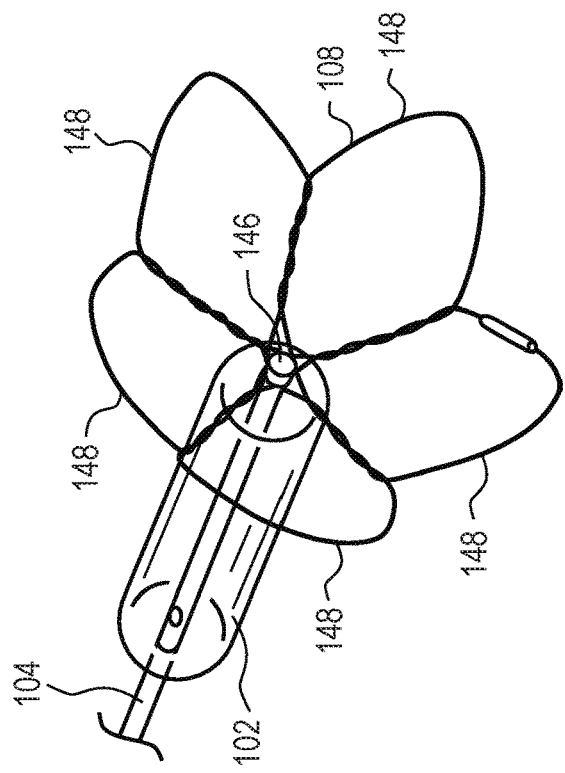
FIGS. 6A and 6B show an exemplary anchor of the system of FIG. 1, where the anchor is contracted within a sheath within a pulmonary artery, or a branch of the pulmonary artery, in FIG. 6A and in an expanded state in FIG. 6B.
Figure 6A:
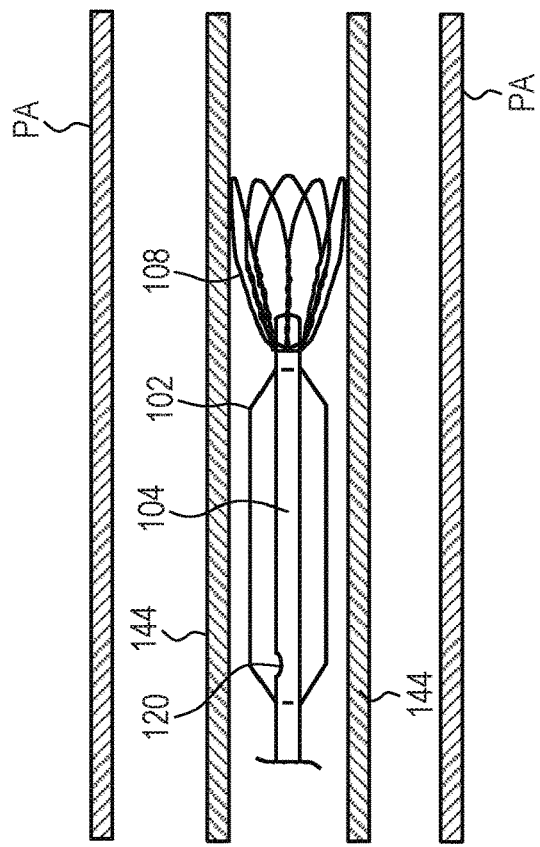

Referring now to FIG. 6A, the distal region of system 100 is shown in a compressed or constrained state within a pulmonary artery PA. Anchor 108 is coupled to conduit 104 between the distal end of compliant body 102 and distal end 146 of conduit 104. Anchor 108 may comprise shape memory material, e.g., nitinol, and is preferably configured to self-expand when exposed from a sheath. Illustratively, anchor 108 includes five petals 148 although more or fewer petals may be used. Preferably, compliant body 102 is in a contracted, deflated state when inserted into the vasculature, and may be implanted either in conjunction with the implantation of the anchor, or subsequent to the implantation of the anchor and then attached to the anchor. After deployment, compliant body 102 may be expanded by introduction of fluid from reservoir 106 through port 120. When compressed within sheath 144, anchor 108 bends distally away from compliant body 102. Anchor 108 is configured to expand to the expanded state when the distal end of sheath 144 is retracted proximally past anchor 108 or when anchor 108 is pushed distally out of the distal end of sheath 144.

In FIG. 6B, a front view of anchor 108 of system 100 in FIG. 1 is provided. In FIG. 6B, anchor 108 is shown in an expanded state. In the expanded state, the distal regions of petals 148 are sized to contact the inner wall of the body lumen, e.g., pulmonary artery, or another anchor deployed within the body lumen. After deployment of anchor 108 and compliant body 102 past the distal end of sheath 144, sheath 144 may be removed from the patient or sheath 144 may be permanently implanted at a position such that the distal end of sheath 144 does not interfere with expansion of compliant body 102 or anchor 108 and the proximal end of sheath 144 does not interfere with coupling the proximal end of conduit 104 to reservoir 106. After deployment, sheath 144, or another similar sheath, may be advanced distally, or conduit 104 pulled proximally, such that compliant body 102 and anchor 108 enter the lumen of sheath 144 at the distal end of sheath 144 to return anchor 108 to the contracted state. Conduit 104 and compliant body 102, including anchor 108, then may be retrieved from sheath 144, e.g., by detaching the proximal end of conduit 104 from reservoir 106 and pulling the proximal end of conduit 104 proximally out the proximal end of sheath 144. If desired, a replacement conduit and/or replacement compliant body may be introduced into the patient through sheath 144 and then attached to reservoir 106 at the proximal end of the replacement conduit.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A system for reducing pulsatile pressure, the system comprising:
   a reservoir configured to hold a fluid therein;
   a transvascular conduit having a proximal region and a distal region, the proximal region coupled to the reservoir; and
   a balloon configured to be implanted in a vessel and coupled to the distal region of the transvascular conduit, the balloon further configured to contract during systole to move the fluid towards the reservoir and to expand during diastole to thereby reduce peak pressure in the vessel, wherein the balloon is formed from a carbon-polymer composite configured to resist diffusion of the fluid through the balloon,
   wherein the carbon-polymer composite comprises a graphene nanoribbon (GNR).

2. The system of claim 1, wherein the balloon is configured for long term implantation in the vessel.

3. The system of claim 1, wherein the balloon is configured to be implanted in a pulmonary artery.

4. The system of claim 1, wherein the carbon-polymer composite comprises at least one of a graphene oxide, a reduced graphene oxide, a graphene nanosheet, a graphene nanoflake, or a graphene nanoplatelet.

5. The system of claim 1, wherein the carbon-polymer composite comprises at least one of a carbon nanotube or a buckminsterfullerene.

6. The system of claim 1, wherein the carbon-polymer composite comprises a graphene-polymer matrix having graphene configured to be compounded into a polymer.

7. The system of claim 1, wherein the carbon-polymer composite comprises graphene configured to be sandwiched between two layers of polymer.

8. The system of claim 1, wherein the carbon-polymer composite comprises graphene configured to be deposited onto at least one of an inner layer and an outer layer of the balloon.

9. The system of claim 8, wherein the carbon-polymer composite comprises graphene configured to be deposited by at least one of dip coating, spraying, rolling, solvent interface trapping, solvent interface dipping, hydro dipping, solution dipping, or powder coating.

10. The system of claim 9, wherein the graphene comprises either graphene alone, or graphene in a liquid or solid suspension.

11. The system of claim 1, wherein the conduit is formed from a carbon-polymer composite configured to resist diffusion of the fluid through the conduit.

12. The system of claim 1, wherein the reservoir comprises a septum configured to allow the addition of fluid to or the removal of fluid from the reservoir and to permit repeated needle penetrations while maintaining a fluid-tight seal.

13. The system of claim 1, wherein the reservoir is formed from a carbon-polymer composite configured to resist diffusion of the fluid through the reservoir.

14. The system of claim 1, wherein the fluid is compressible.

15. The system of claim 1, further comprising an anchor configured to secure the balloon within the vessel.

16. The system of claim 15, wherein the anchor is coupled to the conduit proximal and/or distal to the balloon.

17. The system of claim 1, wherein the balloon comprises a coating material configured to prevent thrombus formation.

18. The system of claim 1, wherein the balloon comprises a lubricious surface configured to impede adhesion of body components.

19. The system of claim 1, wherein the balloon comprises a material configured to minimize chemical or oxidative degradation.

20. A system for reducing pulsatile pressure, the system comprising:
   a reservoir configured to hold a fluid therein;
   a transvascular conduit having a proximal region and a distal region, the proximal region coupled to the reservoir; and
   a balloon configured to be implanted in a vessel and coupled to the distal region of the transvascular conduit, the balloon further configured to contract during systole to move the fluid towards the reservoir and to expand during diastole to thereby reduce peak pressure in the vessel,
   wherein the balloon and at least one of the transvascular conduit or reservoir is formed from a carbon-polymer composite configured to resist diffusion of the fluid through the balloon, transvascular conduit, or reservoir, the carbon-polymer composite comprising a graphene nanoribbon (GNR) with at most 0.5% by weight of GNR.

21. The system of claim 20, wherein the balloon is configured for long term implantation in the vessel.

22. The system of claim 20, wherein the balloon is configured to be implanted in a pulmonary artery.

23. The system of claim 20, wherein the carbon-polymer composite comprises at least one of a graphene oxide, a reduced graphene oxide, a graphene nanosheet, a graphene nanoflake, or a graphene nanoplatelet.

24. The system of claim 20, wherein the carbon-polymer composite comprises a buckminsterfullerene.

25. The system of claim 17, wherein the coating material comprises heparin.

* * * * *